March 19, 1974 H. A. JOHNSON, JR Plant Pat. 3,529
STRAWBERRY PLANT
Filed June 7, 1972
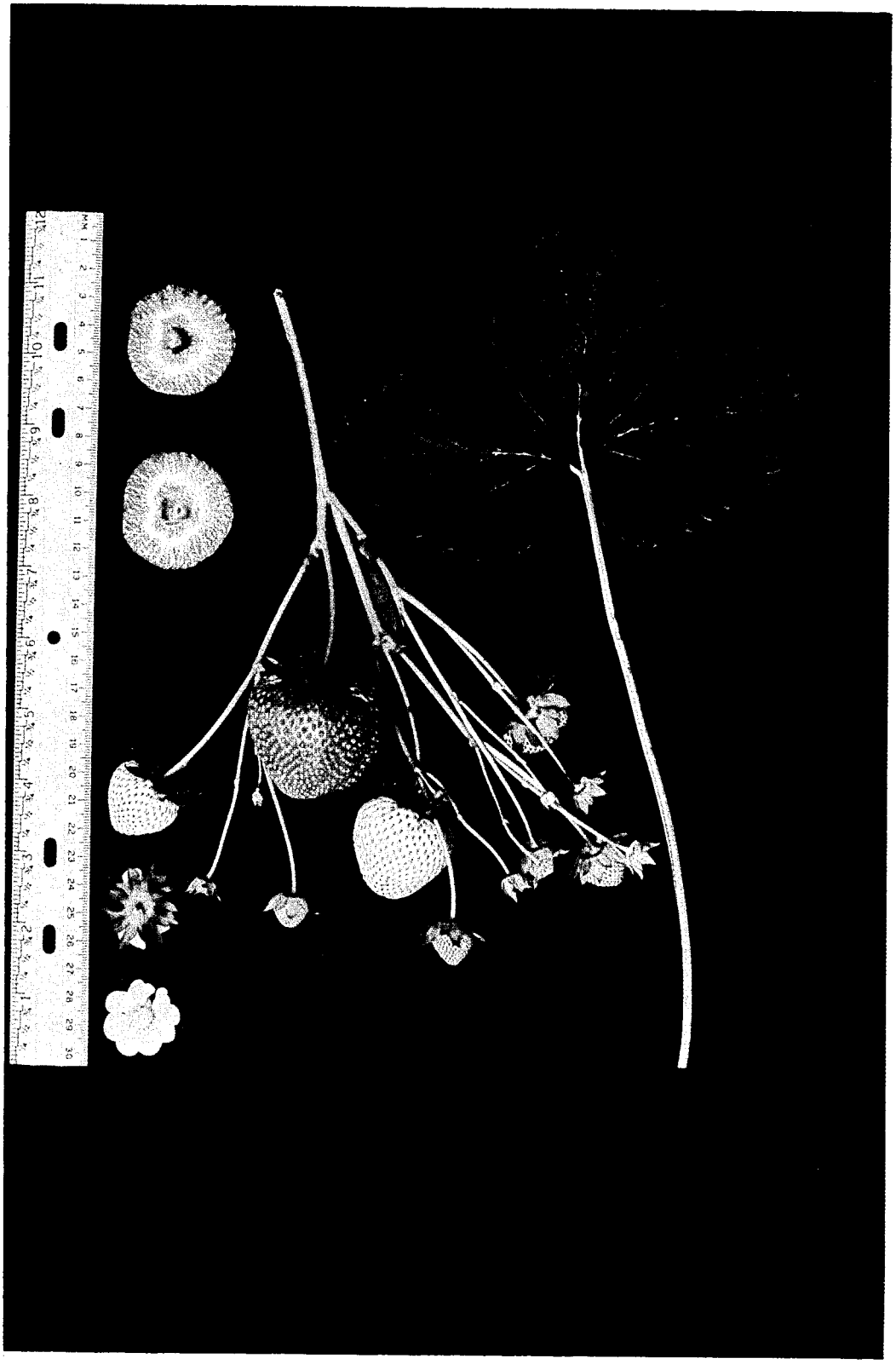

United States Patent Office

Plant Pat. 3,529
Patented Mar. 19, 1974

3,529
STRAWBERRY PLANT

Harold A. Johnson, Jr., Watsonville, Calif., assignor to Driscoll Strawberry Associates, Inc., Watsonville, Calif.

Filed June 7, 1972, Ser. No. 260,694
Int. Cl. A01h 5/03
U.S. Cl. Plt.—49 1 Claim This invention relates to a new and distinct variety of strawberry plant which is the result of a cross of the everbearing Driscoll Strawberry Associates variety R87.18 and the Driscoll Strawberry Associates Goldsmith variety, Pat. No. 1,735.

The seedlings resulting from the aforementioned cross were grown and asexually multiplied in Shasta County, Calif., and tested in the fruiting beds on the property of grower members of Driscoll Strawberry Associates, Inc. Clones of the seedlings were also held at the Propagation Nursery in Shasta County. One plant was selected from the aforementioned group of seedlings and further asexually reproduced in the Shasta County Nursery of Driscoll Strawberry Associates, Inc. Tests followed in various parts of California during intervening seasons on various properties of grower members of the Driscoll Strawberry Associates, Inc. These tests indicated the merits of the novel plant and resulted in its selection as a promising test variety.

Plant parts of the new variety, typical in size, shape and color are pictured in the accompanying photograph. A berry in cross section illustrates flesh color and characteristic core cavity. The inflorescence illustrates typical branching and relative size about the middle of July. The picture shows the presence of three secondary peduncles, with the pedicel holding the primary berry branching from one of the secondary peduncles. The leaf shown is typical in appearance and size but the normal basal bract is missing in this particular picture. The flower pictured is typical of secondary flowers during this period of the year. The novel plant of this everbearing variety is medium in size and vigor. The runner transplant crown is medium to large as it comes from the nursery and produces a vigorous young plant in the spring with crown crop berries of medium size. This variety has the ability to give a large total production even when dug in late January or early February and transplanted in the Central California Coastal region. The transplant does require adequate chilling, however, before it can produce a vigorous enough plant to support a strong spring, summer and fall crop. The primary berries from the crown and main crop are medium to large, uniformly smooth and have an excellent gloss. Subsequent crops and secondary and tertiary fruit are smaller but maintain an acceptable commercial fruit size if the plant maintains adequate vigor. The cropping is continuous after the main crop commences in late May, and continues through late September and October. The crop during the second fruiting year is typical of most everbearers grown in Central California in that it crops later than spring varieties, but maintains production throughout the summer and early fall.

This novel plant of the present invention is distinguished from other varieties by its flowers, fruit and plant characteristics. This plant has the ability to maintain high production and fruit size throughout the season if the plant is given proper chilling and nutrition. It also has the ability to produce firm, high quality fruit during the summer period in soils that are high in nitrogen. This distinguishes this new variety from other varieties such as the Driscoll E4, Plant Pat. No. 2,897, which produces weak fruit and develops a physiological condition described in strawberry literature as albinism when the plants are growing in mid-summer under high levels of nitrates in the soil. The plant is similar to the E4 variety in size, but the new variety may become larger when grown on some soil types. The new variety produces a plant with multiple crowns similar to E4, but this is in contrast to the Driscoll E2 variety, Plant Pat. 2,611, which produces a more open plant with fewer crowns per plant than the new variety. The leaf size of the new variety is similar to that of E4, but not as large as E2. The leaves are cupped upward slightly in the new variety, but not to the extent of the E4. The petioles of the new variety and E4 are directed upward while those of the E2 are more prostrate. The length of the petiolule of the center leaflet is considered long and is longer than that produced by the E4 variety. The new variety produces many inflorescences per plant during the mid-summer fruiting period, similar to E4 and the average length of individual inflorescences is slightly longer than the E4. Flowers are usually noticeably visible above the plant early in the season but not after the spring or late summer cropping. The length of the common peduncle is also longer than that of E4. The number of petals per flower, as well as the average diameter of a primary is normally greater than that of E4. Normally the pedicel holding the primary berry originates at the axil of secondary peduncles, but a small percentage branch from one of the secondary peduncles and in this respect is similar to that which occurs on the E4 variety. When plant vigor is maintained the fruit size of the new variety is equal to, to slightly larger than E4. The length of primaries is equal to, to slightly larger than the width. The fruit surface of the new variety is more uniformly smooth, less irregular in shape, darker and more consistent in color, more glossy and the seeds are more exerted than E4. These exerted seeds may give the fruit a seedy appearance at times. Primary berries of the E2 variety are usually larger but more prone to be malshaped and are not as firm as the new variety. The calyx of the new variety is larger in diameter and the number of sepals is slightly more than that of E4. The individual sepals on the new variety are larger, more overlapped and produce more serrations than occurs on E4. Individual sepals of the new variety tend to lay close to the fruit, but may become reflexed at times as is shown in the illustration of a ripe berry. The fruit shape of the new variety is mostly short to medium wedge but may become conic as described in the U.S.D.A. Bulletin No. 1043. The flesh and epidermis are both firm in this new berry which is a distinct character that makes it a valuable variety for interstate shipment. The dessert quality of this variety is good, superior to E2 and E4. There is generally no aroma peculiar to the flesh of this new variety. This new variety appears to be less tolerant to the two-spotted mite than E4, but is able to tolerate moderate populations. It is also moderately susceptible to mildew, as well as to Mycrosphaerella leaf spot during wet spring periods. It has not been completely tested against the Verticillium and Red Stele diseases. As a seedling and selection, this variety withstood the natural invasions of certain virus components found in Central California without losing its ability to produce.

The varietal characteristics of the novel plant, described below in detail, were observed mainly during the first fruiting season, but reference is also made to the appearance during the second fruiting year. Observations were made in the Watsonville area of California which is a cool coastal area near the Pacific Ocean. The color terminology is in accordance with Ridgeways Color Standard and Nomenclature (1912 edition).

Plants: Medium, vigorous if given ample chilling before being planted and given adequate soil nutrition and has an extensive root system, producing multiple crowns by the end of the first fruiting season.

Leaves: Medium in size. Central leaflet is usually 4½ to 6 cm. wide and 5 to 6½ cm. in length. Petioles abundant and long for an everbearer. Petiolules are long and often over 10 mm. in length. Bracts are not generally present on the petioles. Leaflet shape may vary, mostly eliptical and obtuse but often becoming ovate. Leaflet color may vary during the season with the darker leaves becoming lighter as the season progresses. The upper side of the leaflet is Yew Green, Plate XXXI. Leaflets may be cupped up moderately from the main vein to the apex of the serrations, not cupped up at the marginal serrations only.

Runners: Vigorous, but erratic in production both at the nursery and in the fruiting beds.

Inflorescence: Medium in length, averaging 15 to 25 cm. during late summer. Common peduncle is medium in length, mostly 8 to 12 cm. Secondary peduncles are mostly two, but may be three or four in number. Primary berries usually ripen before secondary. Secondary berries are smaller than primaries but the variation in size is not great. Diameter of primary flowers is medium to large, 30 to 35 cm. Petals on leaflets are abundant, five to eight in number. Pedicels holding primary berry originate mainly at axil of secondary peduncles but may also branch from one of the peduncles near the axil. Anthers produce an abundance of pollen except during the early spring period.

Fruit: Crown crop berries are small to medium but usually meet commercial shipping standards if the plant is vigorous. The main crop is mostly uniformly medium in size. Primaries are mainly 35 mm. in length with the width slightly less during the late summer. Shape of fruit is mainly short to medium wedge with some becoming medium conic. Fruit surface is uniform, not ridged or malformed. Shoulders are rounded at the calyx end of the fruit and not necked. The fruit appears to be susceptible to spray injury, especially during warm weather. Flesh and epidermis are firm and seeds are slightly exerted. Seeds are medium in size and remain yellow except where fully exposed to the sun. The berry has a high dessert quality when ripe. The fruit surface color is Scarlet Red, Plate I, and the core color is Peach Red, Plate I and Scarlet near surface, Plate I. Fruit surface color is uniform and maintains a high gloss even after a long shipment and storage.

Calyx: Large in diameter in relationship to fruit size, averaging 35 mm. to 40 mm. during late summer. The calyx is usually held irregularly near the fruit surface but may become reflexed. Sepals mostly overlap and are abundant. Sepals vary from elliptical to ovate or obovate and usually have serrations.

I claim:

1. A new and distinct variety of strawberry plant herein described and illustrated, and identified by the characteristics enumerated above.

No references cited.

ROBERT E. BAGWILL, Primary Examiner